United States Patent [19]

Jett et al.

[11] Patent Number: 4,962,037

[45] Date of Patent: Oct. 9, 1990

[54] METHOD FOR RAPID BASE SEQUENCING IN DNA AND RNA

[75] Inventors: James H. Jett; Richard A. Keller; John C. Martin; Robert K. Moyzis; Robert L. Ratliff; E. Brooks Shera; Carleton C. Stewart, all of Los Alamos, N. Mex.

[73] Assignee: United States of America, Washington, D.C.

[21] Appl. No.: 105,375

[22] Filed: Oct. 7, 1987

[51] Int. Cl.$^5$ .............................................. C12Q 1/68
[52] U.S. Cl. ........................................ 435/6; 435/41; 435/75; 436/501; 436/94; 436/175; 436/800; 935/77; 935/78
[58] Field of Search ............... 435/6, 41, 75; 436/501, 436/94, 175, 800; 935/77, 78

[56] References Cited

U.S. PATENT DOCUMENTS 3,730,844  5/1973  Gilham et al.
4,521,509  6/1985  Benkovic et al.

FOREIGN PATENT DOCUMENTS 0251575  1/1988  European Pat. Off.

OTHER PUBLICATIONS

Baumlein et al., (1986) Nucleic Acids Research 14(6):2707–2720.
Shimkus et al., *DNA*, 5:247 (1986).

*Primary Examiner*—Amelia Burgess Yarbrough
*Attorney, Agent, or Firm*—Irell & Manella

[57] ABSTRACT

A method is provided for the rapid base sequencing of DNA or RNA fragments wherein a single fragment of DNA or RNA is provided with identifiable bases and suspended in a moving flow stream. An exonuclease sequentially cleaves individual bases from the end of the suspended fragment. The moving flow stream maintains the cleaved bases in an orderly train for subsequent detection and identification. In a particular embodiment, individual bases forming the DNA or RNA fragments are individually tagged with a characteristic fluorescent dye. The train of bases is then excited to fluorescence with an output spectrum characteristic of the individual bases. Accordingly, the base sequence of the original DNA or RNA fragment can be reconstructed.

21 Claims, 1 Drawing Sheet

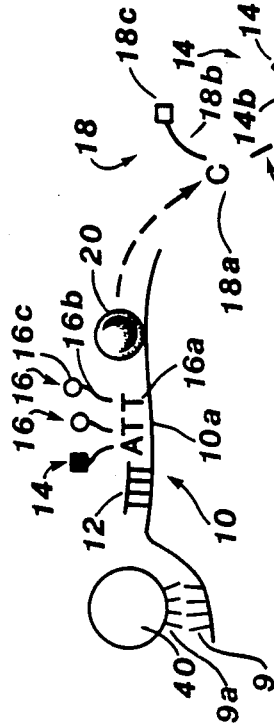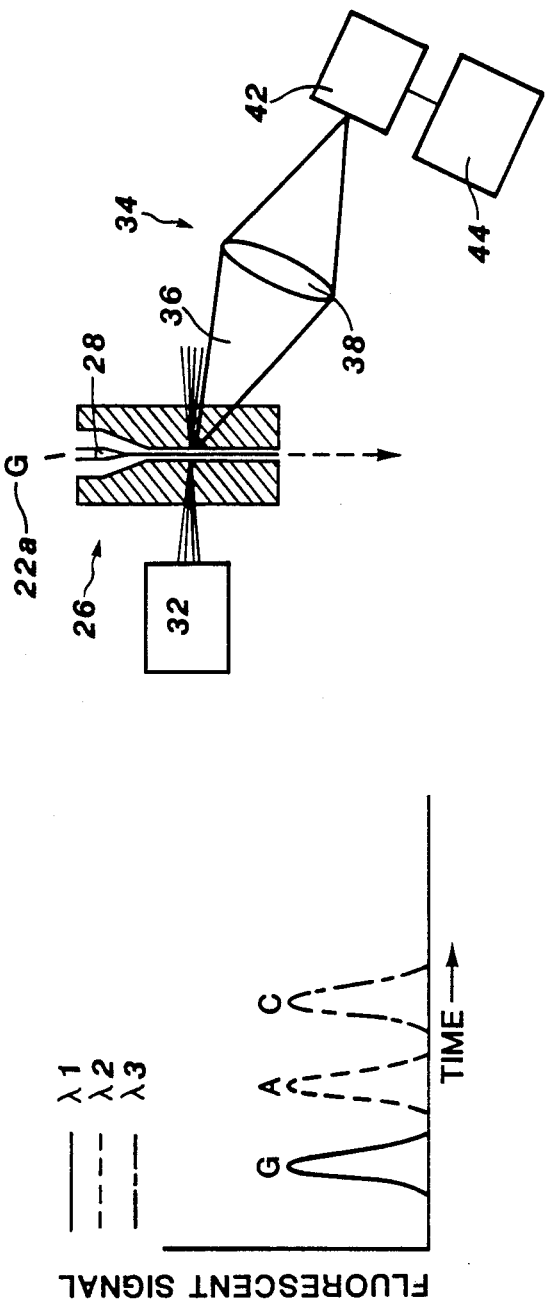
Fig. 1
Fig. 2

METHOD FOR RAPID BASE SEQUENCING IN DNA AND RNA

This invention is the result of a contract with the Department of Energy (Contract No. W-7405ENG-36)

BACKGROUND OF THE INVENTION

This invention is generally related to DNA and RNA sequencing and, more particularly, to DNA and RNA sequencing by detecting individual nucleotides.

A world-wide effort is now in progress to analyze the base sequence in the human genome. The magnitude of this task is apparent, with $3 \times 10^9$ bases in the human genome, and available base sequencing rates are about 200–500 bases per 10–24 hour period. Considerable interest also exists in nucleic acid sequencing from non-human sources. Existing procedures are labor intensive and cost approximately $1 per base.

By way of example, Sanger et al., "DNA Sequencing with Chain-Terminating Inhibitors," proceedings of the National Academy of Science, USA 74, 5463-7 (1977) provide for sequencing 1–200 nucleotides from a priming site. Radioactive phosphorus is used in the primer extension to provide a marker. Enzymatic resynthesis coupled with chain terminating precursors are used to produce DNA fragments which terminate randomly at one of the four DNA bases adenine (A), cytosine (C), guanine (G), or thymine (T). The four sets of reaction products are separated electrophorectically in adjacent lanes of a polyacrylamide gel. The migration of the DNA fragments is visualized by the action of the radioactivity on a photographic film. Careful interpretation of the resulting band patterns is required for sequence analysis This process typically takes 1–3 days. Further, there are problems with band pile-ups in the gel, requiring further confirmatory sequencing.

In a related technique, A. M. Maxam and W. Gilbert, "A New Method for Sequencing DNA," proceedings of the National Academy of Science USA 74 560-564 (1977), teach a chemical method to break the DNA into four sets of random length fragments, each with a defined termination. Analysis of the fragments proceeds by electrophoresis as described above. The results obtained using this method are essentially the same as the "Sanger Method."

In another example, Smith et al., "Fluorescent Detection in Automated DNA Sequence Analysis," Nature 321, 674-679 (June 1986), teach a method for partial automation of DNA sequence analysis. Four fluorescent dyes are provided to individually label DNA primers. The Sanger method is used to produce four sets of DNA fragments which terminate at one of the four DNA bases with each set characterized by one of the four dyes. The four sets of reaction products, each containing many identical DNA fragments, are mixed together and placed on a polyacrylamide gel column. Laser excitation is then used to identify and characterize the migration bands of the labeled DNA fragments on the column where the observed spectral properties of the fluorescence are used to identify the terminal base on each fragment. Sequencing fragments of up to 400 bases has been reported. Data reliability can be a problem since it is difficult to uniquely discern the spectral identity of the fluorescent peaks.

These and other problems in the prior art are addressed by the present invention and an improved process is provided for rapid sequencing of DNA bases. As herein described, the present invention provides for the sequential detection of individual nucleotides cleaved from a single DNA or RNA fragment.

Accordingly it is an object of the present invention to provide an automated base sequence analysis for DNA and RNA.

Another object of the present invention is to process long strands of DNA or RNA, i.e., having thousands of bases.

One other object is to rapidly sequence and identify individual bases.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention as embodied and broadly described herein, a method for DNA and RNA base sequencing is provided. A single fragment from a strand of DNA or RNA is suspended in a moving sample stream. Using an exonuclease, the end base on the DNA or RNA fragment is repetitively cleaved from the fragment to form a train of the bases in the sample stream. The bases are thereafter detected in sequential passage through a detector to reconstruct the base sequence of the DNA or RNA fragment.

In another characterization of the present invention, strands of DNA or RNA are formed from the constituent bases, which have identifiable characteristics. The bases are sequentially cleaved from the end of a single fragment of the strands to form a train of the identifiable bases. The single, cleaved bases in the train are then sequentially identified to reconstruct the base sequence of the DNA or RNA strand.

In one particular characterization of the invention, each of the nucleotides effective for DNA and RNA resynthesis is modified to possess an identifiable characteristic. A strand of DNA is synthesized from the modified nucleotides, where the synthesized strand is complementary to a DNA or RNA strand having a base sequence to be determined. A single fragment of the complementary DNA or RNA is selected and suspended in a flowing sample stream. Individual identifiable nucleotides are sequentially cleaved from the free end of the suspended DNA strand. The single bases are then sequentially identified. The base sequence of the parent DNA or RNA strand can then be determined from the complementary strand base sequence.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings:

FIG. 1 is a graphic illustration of a DNA sequencing process according to the present invention.

FIG. 2 is a graphical representation of an output signal according to the present invention.

DETAILED DESCRIPTION OF THE INVENTION

According to the present invention, a method is provided for sequencing the bases in large DNA or RNA fragments by isolating single DNA or RNA fragments in a moving stream and then individually cleaving single bases into the flow stream, forming a sequence of the bases through a detection device. In one embodiment the single bases in the flowing sample streams are interrogated by laser-induced fluorescence to determine the presence and identity of each base.

It will be understood that DNA and RNA strands are each formed from nucleotides comprising one of four organic bases: adenine, cytosine, quanine, and thymine (DNA) or uracil (RNA). The DNA and RNA nucleotides are similar, but not identical: however, the nucleotides and strands of nucleotides can be functionally manipulated in a substantially identical manner. Also, the complement of an RNA fragment is conventionally formed as a DNA strand with thymine in place of uracil. The following description is referenced to DNA sequencing, but any reference to DNA includes reference to both DNA and RNA and without any limitation to DNA.

In a particular embodiment of the present invention, the initial step is an enzymatic synthesis of a strand of DNA, complementary to a fragment to be sequenced, with each base containing a fluorescent tag characteristic of the base. Sequencing the complementary strand is equivalent to sequencing the original fragment. The synthesized strand is then suspended in a flowing sample stream containing an exonuclease to cleave bases sequentially from the free end of the suspended DNA or RNA. The cleaved, fluorescently labeled bases then pass through a focused laser beam and are individually detected and identified by laser-induced fluorescence.

The maximum rate that bases may be sequenced is determined by the kinetics of the exonuclease reaction with DNA or RNA and the rate of detection. A projected rate of 1000 bases/sec would result in sequencing $8 \times 10^7$ bases/day. This is in contrast to standard techniques which take 10–24 hours to sequence 200–500 bases.

Referring now to FIG. 1, one effective sequencing method comprises the following steps; (1) prepare a selected strand of DNA 10 in which individual bases are provided with an identifiable characteristic, e.g., labeled with color-coded fluorescent tags to enable each of the four bases to be identified (2) select and suspend 40 a single fragment of DNA with identifiable bases in a flowing sample stream, (3) sequentially cleave 20 the identifiable bases from the free end of the suspended DNA fragment, and (4) identify the individual bases in sequence, e.g., detect 34 the single, fluorescently labeled bases as they flow through a focused laser system. Exemplary embodiments of the individual process steps are hereinafter discussed.

Selection of DNA Fragment to be Sequenced

In accordance with the present process, a single DNA fragment 10a is selected and prepared for labeling and analysis. In an exemplary selection process from a heterogeneous mixture of DNA fragments, avidin is bound to microspheres and a biotinylated probe, complementary to some sequence within the desired DNA fragment 10a, is bound to the avidin on the microspheres. The avidin-biotinylated probe complex is then mixed with the heterogeneous mixture of DNA fragments to hybridize with the desired fragments 10a. The beads are separated from the unbound fragments and washed to provide the desired homogeneous DNA fragments 10a.

The selected fragments are further processed by removing the first microsphere and ligating a tail of known sequence 9 to the primer 12 attached to the 3' end of the fragment 10a. Microspheres 40 are prepared with phycoerythrin-avidin and sorted to contain a single molecule of phycoerythrin-avidin. A single complementary probe 9a to the known sequence 9 is biotinylated and bound to the sorted microspheres 40. The bead-probe complex is then hybridized to the selected fragment 10a. Thus, a single fragment of DNA 10a will be bound to each microsphere.

In another embodiment, a homogeneous source of DNA fragments is provided. e.g. from a gene library. A selection step is not then required and the homogeneous DNA fragments can be hybridized with the microspheres 40 containing a single molecule of phycoerythrin-avidin, with the appropriate complementary probe attached as above.

In either case, a single microsphere 40 can now be manipulated using, for example, a microinjection pipette to transfer a single fragment strand for labeling and analysis as discussed below.

Fluorescence Labeling Bases

The bases forming the single fragment to be analyzed are provided with identifiable characteristics. The identifiable characteristic may attach directly to each nucleotide of DNA strand 10a. Alternatively, bases may first be modified to obtain individual identifiable characteristics and resynthesized to selected strand 10a to form a complementary DNA strand. In either event, DNA fragment 10 is provided for analysis with identifiable bases.

In one embodiment, a fluorescent characteristic is provided. The bases found in DNA do have intrinsic fluorescence quantum yields $<10^{-3}$ at room temperature. In order to detect these bases by a fluorescence technique however, it is desirable to modify them to form species with large fluorescence quantum yields and distinguishable spectral properties, i.e., label the bases.

Methods for synthesizing a complementary strand of DNA by an enzymatic procedure using labeled nucleotides in which the labels are attached to the nucleotides via linker arms are known in the art. See, e.g., p. R. Langer et al., "Enzymatic Synthesis of Biotin-Labeled polynucleotides: Novel Nucleic Acid Affinity probes," proc, Natl. Aca. Sci. USA 78, 6633 (1981); M. L. Shimkus et al., "Synthesis and Characterization of Biotin-Labeled Nucleotide Analogs." DNA 5, 247 (1986); all incorporated herein by reference. Referring to FIG. 1, a primer 12 is attached to the 3' end of a DNA fragment 10a and an enzyme, e.g., DNA polymerase-Klenow fragment, is used to synthesize the complement to DNA fragment 10a starting from the end of primer 12. Modified deoxynucleotides 14, 16, 18, 22 are used in the synthesis (typically modified dATp 14a, dTTp (or dUTp) 16a, dCTp 18a, and dGTp 22a).

Each of the modified nucleotides is formed with a long carbon chain linker arm 14b, 16b, 18b, and 22b, respectively, terminating in a characteristic fluorescent dye 14c, 16c, 18c, and 22c. The modified nucleotides 14, 16, 18, and 22 are then incorporated into the synthesized fragment by DNA polymerase. The long linker arms 14b, 16b, 18b, 22b isolate the fluorescent dye tags 14c, 16c, 18c, 22c from the bases 14a, 16a, 18a, 22a to permit uninhibited enzyme activity.

DNA fragments several kB long have been synthesized with each base containing a carbon chain linker arm terminating in biotin as hereinafter described. To exemplify the DNA synthesis, tagging, and cleaving processes a known strand of DNA nucleotides was formed, nucleotides were tagged with a linker arm terminating in biotin, and a complementary strand of DNA was synthesized from the tagged nucleotides. Biotin was used as a model tag rather than fluorescent dyes to demonstrate the synthesis and cleavage reactions.

1. preparation of known strand [d(A.G)]:

A polydeoxynucleotide, $d(A,G)_{2138}$, was prepared by the method outlined in R. L. Ratliff et al., "Heteropolynucleotide Synthesis with Terminal Deoxyribonucleotidyltransferase," Biochemistry 6, 851 (1967) and "Heteropolynucleotides Synthesized with Terminal Deoxyribonucleotidyltransferase, II. Nearest Neighbor Frequencies and Extent of Digestion by Micrococcal Deoxyribonuclease," Biochemistry 7, 412 (1968). The subscript, 2138, refers to the average number of bases in the fragment and the comma between the A and the G indicates that the bases are incorporated in a random order.

Ten micromoles of the 5'-triphosphate of 2'-deoxyadenosine (dATp) were mixed with one micromole of the 5'-triphosphate of 2'-deoxyguanosine (dGTp) and 5.5 nanomoles of the linear heptamer of 5'-thymidylic acid $[d(pT)_7]$ which acts as a primer. Ten thousand units of terminal transferase were added to the solution which was buffered at pH 7 and the reaction mixture was maintained at 37° C. for 24 hours. (One unit is defined as the amount of enzyme which will polymerize 1 nanomole of nucleotide in one hour.) The resulting $d(A.G)_{2138}$ was then separated from the reaction mixture and purified.

2. preparation of biotinylated complementary strand $[d(C.U)_{2138}]$:

The complementary strand of DNA to $d(A.G)_{2138}$, prepared as described above, was synthesized from nucleotides (dCTp) and d(UTp) tagged with biotin. A mixture of 10 nanomoles of the biotinylated 5'-triphosphate of 2'-deoxycytidine (dCTp) and 20 nanomoles of the biotinylated 5'-triphosphate of 2'-deoxyuridine (dUTp) was added to 10 nanomoles of $d(A,G)_{2138}$ and 22 picomoles of $d(pT)_7$. Ten units of DNA polymerase (E coli). Klenow fragment, were then added to the mixture which was buffered at pH 8 and maintained at a temperature of 37° C. for 2 hours. Analysis of the resulting products by electrophoresis demonstrated that the reaction went to completion and the completely biotinylated complementary DNA fragment. $d(C.U)_{2138}$, was formed.

3. Exonuclease cleavage of biotinylated $d(C.U)_{2138}$:

The completely biotinylated $d(C.U)_{2138}$, synthesized as described above, was sequentially cleaved by adding 10 units of exonuclease III to 5 nanomoles of $d(A.G)_{2138}$, biotinylated $d(C,U)_{2138}$. The reaction mixture was maintained at pH 8 and 37° C. for two hours. At the end of two hours, analysis of the reaction mixture showed that 30% of the DNA was cleaved and the cleavage reaction appeared to be still proceeding. A control reaction using normal $d(C.T)_{2138}$ yielded 85% cleavage in two hours. Hence, biotinylation does appear to slow the cleavage reaction using exonuclease III, but the tagged nucleotides were sequentially cleaved from the DNA fragments.

In accordance with the present invention, the selected fluorescent dyes are substituted for biotin to specifically tag each nucleotide type with a dye characteristic of that nucleotide. The resulting complementary DNA chain will then provide each base with a characteristic, strongly fluorescing dye. By way of example, Smith et al,, supra, teach a set of four individually distinguishable tags.

The sensitivity for fluorescence detection can be increased, if necessary, by attaching several dye molecules along the linker arm. Alternatively, large phycoerythrin-like molecules or even small microspheres containing many dye molecules may be attached to the linker arm. In yet another alternative, fluorescent labels might be attached to the primary, single stranded fragment, thereby eliminating the necessity of forming labeled bases and synthesizing the complementary strand.

It should be noted that DNA fragment 10 may be either a single or double strand of DNA. A single strand of DNA arises where the selected DNA strand is directly tagged for base identification or where the resynthesized complementary tagged DNA strand is separated from the selected strand. A double strand arises where the resynthesized DNA strand remains combined with the selected strand. As used herein, the term "fragment" refers to any and all of such conditions.

Enzymatic Cleavage of the Tagged Nucleotides

After DNA fragment 10 is formed with identifiable bases and hybridized to microsphere 40, a single fragment 10 can be manipulated with microsphere 40 and suspended in flow stream 24. Exonuclease 20 is used to cleave bases 14a, 16a, 18a, 22a sequentially from single DNA fragment 10 suspended in flow stream 24. While the presence of the linker arm and the fluorescent dye may inhibit the enzymatic activity of some exonucleases, suitable exonucleases will cleave with only a slight reduction in rate. Individual bases have been sequentially enzymatically cleaved from DNA fragments formed completely from biotinylated nucleotides as demonstrated above. See, also, e.g., M. L. Shimkus et al., supra, incorporated herein by reference. The rate of cleavage can be adjusted by varying the exonuclease concentration, temperature, or by the use of poisoning agents. The time to remove one base can be made to be on the order of one millisecond. See, e.g., W. E. Razzell et al., "Studies on polynucleotides," J. Bio. Chem. 234 No 8, 2105–2112 (1959).

Single Molecule Detection

The individual modified nucleotides 14, 16, 18, and 22 are carried by flow stream 24 into flow cell 26 for detection and analysis by single molecule detection system 34. One embodiment of a laser-induced fluorescence detection system is described in D. C. Nguyen et al., "Ultrasensitive Laser-Induced Fluorescence Detection in Hydrodynamically Focused Flows." J. Opt. Soc. Am. B, 4, 138–143, No. 2 (1987), incorporated herein by reference. The photomultiplier-based detection system described therein has detected single molecules of phycoerythrin in focused, flowing sample streams by laser-induced fluorescence. See D. C. Nguyen et al., "Detection of Single Molecules of phycoerythrin in Hydrodynamically Focused Flows by Laser-Induced Fluorescence," Anal. Chem. 59, 2158–2161 (September 1987), incorporated herein by reference.

Phycoerythrin is a large protein containing the equivalent of 25 rhodamine-6G dye molecules. The detection of single molecules/chromophores of rhodamine-6G and equivalent dye molecules is suggested by system improvements. Thus, a combination of improved light collection efficiency improved detector quantum efficiency, or pulsed excitation and gated detection to reduce background noise can be used with the Nguyen et al. system. Detection of phycoerythrin was accomplished in the 180 µs it took the molecule to flow through the focused laser beam.

In a preferred embodiment of the present process, the hydrodynamically focused flow system of Nguyen et al, is provided with an improved fluorescence detection system described in a copending patent application by Shera, "Single Molecule Tracking," Docket No. 65,737, incorporated herein by reference. As therein described, flow stream 24 provides to flow cell 26 modified nucleotides 14, 16, and 22 in the sequence they are cleaved from DNA strand 10. Laser system 32 excites fluorescent dyes 14c, 16c, 18c and 22c at selected wavelengths for identification in laminar sample flow 28 within flow cell 26.

Fluorescent events contained in optical signal 36 are focused by lens 38 on position sensitive detector system 42. Detector system 42 may comprise a microchannel plate (MCp) sensor to output spatial coordinates of observed photon events. An internal clock provides a temporal coordinate, wherein data processor 44 determines the presence of a molecule within flow cell 26. Molecular spectral response to laser 32 excitation enables the specific modified nucleotide to be identified. As noted by Shera, supra, data handling in the single molecule detection system 34 effectively provides a moving sample volume within focused flow stream 28 which contains only a single tagged nucleotide. System 34 can thus track multiple molecules existing within focused flow stream 28 to enable a high rate of sequencing to be maintained.

Referring now to FIG. 2, there is shown a representative output signal from the single molecule detection system. The individual nucleotide molecules 14 16, 18, and 22 are individually cleaved from DNA strand 10 into flow stream 24. The flow velocity and laminar flow conditions maintain the molecules in a train for sequential passage through flow cell 26 and the emitted photons from laser-excited molecular fluorescence are assigned to individual molecules passing within the cell. The characteristic dye for each type nucleotide is selected to have an identifiable excitation or fluorescence spectrum. This characteristic spectrum can be used to establish the base sequence for the DNA strand being investigated.

It will be appreciated that the present process further provides a capability to sort the detected molecules and deposit them on a moving substrate for subsequent identification, e.g., as described in M. R. Melamed et al., "Flow Cytometry and Sorting," Wiley, New York (1979), incorporated herein by reference. The flow stream maintains the bases spatially isolated in a flow stream for presentation to a secondary identification device. The position between molecules on the moving substrate can be adjustable and can be large enough to resolve the sorted molecules by other techniques.

The foregoing description of the preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for DNA and RNA base sequencing, comprising the steps of:
    isolating a single fragment of DNA or RNA;
    introducing said single fragment into a moving sample stream;
    sequentially cleaving the end base from the DNA or RNA fragment with exonuclease to form a train of said bases; and
    detecting said bases in said train in sequential passage through a detector which detects single molecules.

2. A method according to claim 1, wherein each said base of said single fragment is modified to contain a tag having an identifiable characteristic for said base.

3. A method according to claim 2, where said bases are modified prior to said cleavage.

4. A method according to claim 2 further including the step of enzymatically synthesizing a strand of DNA complementary to a DNA or RNA strand to be characterized, where each nucleotide forming said synthesized strand contains a tag characteristic of that nucleotide.

5. A method according to claim 2, wherein said tag is separated from the nucleotide by a linker arm effective for said cleavage.

6. A method according to claim 1, wherein said cleaved bases are detected optically.

7. A method according to claim 6, wherein each said tag is a fluorescent dye characteristic of one type of said nucleotides.

8. A method according to claim 7, further including the step of exciting each said fluorescent dye and detecting the fluorescence spectrum of said dye.

9. A method according to claim 1 wherein said step of isolating said single fragment of DNA or RNA includes the step of hybridizing said fragment to a substrate having a site effective for said hybridization.

10. A method according to claim 9, further including the step of selecting said DNA or RNA fragments from a heterogeneous collection of DNA or RNA fragments wherein said site is a biotinylated probe effective to hybridize with DNA or RNA fragments to be selected.

11. A method according to claim 9, wherein said isolating said single fragment includes the step of providing said substrate with a single site effective to hybridize with a single DNA fragment.

12. A method for base sequencing of DNA or RNA fragments, comprising the steps of:
    forming said fragments with bases having identifiable characteristics;
    sequentially cleaving single identifiable bases from a single one of said fragments to form a train of said identifiable bases; and
    identifying said single, cleaved bases in said train.

13. A method according to claim 12, further including the step of attaching a characteristic identifiable fluorescent dye to each said base.

14. A method according to claim 12, wherein the steps of forming said fragments includes the steps of forming by enzymatic synthesis a complementary strand of said DNA or RNA to be sequenced from said bases having identifiable characteristics and thereafter base sequencing said complementary strand.

15. A method according to claim 14, further including the step of attaching a characteristic identifiable fluorescent dye to each said base.

16. A method according to claim 13, wherein said step of identifying said single, cleaved bases includes the step of exciting each said fluorescent dye and detecting the fluorescence spectrum of said dye.

17. A method according to claim 15, wherein said step of identifying said single, cleaved bases includes the step of exciting each said fluorescent dye and detecting the fluorescence spectrum of said dye.

18. A method for DNA or RNA base sequencing, comprising the steps of;
   modifying each nucleotide effective for DNA or RNA synthesis to attach a fluorescent dye characteristic of that nucleotide with a linker arm effective to enable DNA or RNA synthesis and exonuclease cleavage;
   synthesizing from said modified nucleotides a strand of DNA complementary to a DNA or RNA strand having a base sequence to be determined;
   cleaving each said modified nucleotide sequentially from a single fragment containing said complementary DNA strand; and
   fluorescing each said characteristic dye to identify said sequence of nucleotides.

19. A method according to claim 18, wherein the step of fluorescing said dyes further comprises the steps of:
   exciting each said modified nucleotide with a laser effective to fluoresce said characteristic dye; and
   detecting said fluorescence to sequentially identify said nucleotides and generate said sequence of said DNA or RNA.

20. A method according to claim 18, further including the step of suspending a single fragment of synthesized DNA or RNA strand in a laminar flow stream.

21. A method according to claim 18, wherein each synthesized DNA or RNA fragment is manipulated by hybridizing said fragment to a microsphere having a site effective for hybridization.

* * * * *